United States Patent
Franke et al.

(10) Patent No.: US 6,987,190 B2
(45) Date of Patent: Jan. 17, 2006

(54) METHOD FOR THE CONTINUOUS PRODUCTION OF ACETYLENE DIUREA

(75) Inventors: Dirk Franke, Birkenheide (DE); Klaus Horchler, Limburgerhof (DE); Vilmos Czikkely, Mannheim (DE)

(73) Assignee: COMPO GmbH & Co. KG, Münster (DE)

( * ) Notice: Subject to any disclaimer, the term of this patent is extended or adjusted under 35 U.S.C. 154(b) by 308 days.

(21) Appl. No.: 10/614,556

(22) Filed: Jul. 7, 2003

(65) Prior Publication Data
US 2004/0054191 A1    Mar. 18, 2004

(30) Foreign Application Priority Data
Jul. 6, 2002    (DE) ................................ 102 30 490

(51) Int. Cl.
*C07D 403/02*    (2006.01)

(52) U.S. Cl. ................................... 548/303.4
(58) Field of Classification Search ............. 548/303.4
See application file for complete search history.

(56) References Cited

U.S. PATENT DOCUMENTS

| | | |
|---|---|---|
| 2,731,472 A | 6/1956 | Reibnitz |
| 2,803,564 A | 8/1957 | Gagarine et al. |
| 3,061,423 A | 10/1962 | Symes et al. |

FOREIGN PATENT DOCUMENTS

| | | |
|---|---|---|
| JP | 2000 264887 | 9/2000 |
| JP | 2000 290281 | 10/2000 |
| JP | 2001 097974 | 4/2001 |

OTHER PUBLICATIONS

Ann. Chem. 333, (1904) pp 101 to 111.
Chem. Inc. 1979, p. 29 to 30.
Soil Sci. Plant. Nutr. 33 (1987, pp. 291 to 298).
Chemistry and Industry, Jan. 1979, pp. 29 to 30 (Glycoluril as a slow-release nitrogen source for plants).
Abstract XP-002250668 "*Glycoluril as a slow release nitrogen fertilizer*" Shimizu, Toshio. Chemical Abstract Service. Soil Science and Plant Nutrition (Tokyo, Japan) (1987), 33(2), 291-298.
Abstract XP-002250669 Section Ch, Week 200114, Derwent Publication Class C02, AN 2001-127343 JP 2000 290281 A (Mitsui Chem Inc.), Oct. 17, 2000.

*Primary Examiner*—Kamal A. Saeed
(74) *Attorney, Agent, or Firm*—Collard & Roe, P.C.

(57) ABSTRACT

The continuous production of acetylene diurea takes place by means of the reaction of glyoxal with urea in the presence of mineral acids. The reaction is carried out in at least one reactor having a mixing device, into which glyoxal, urea, and mineral acid are continuously fed, and from which a suspension of acetylene diurea in mother liquor is discharged. The acetylene diurea is mechanically removed from the mother liquor, and the remaining mother liquor is recycled back into the reactor, in whole or in part.

10 Claims, No Drawings

METHOD FOR THE CONTINUOUS PRODUCTION OF ACETYLENE DIUREA

BACKGROUND OF THE INVENTION

1. Field of the Invention

The present invention relates to a method for the continuous production of the time-release nitrogen fertilizer acetylene diurea.

2. The Prior Art

Fertilizers with a time-release effect have many advantages as compared with conventional mineral or organic fertilizers. They offer a delivery of nutrients to the plants that is better in keeping with the plants' needs, and thereby improve the utilization of the nutrients. This results in a reduction in nutrient losses, thereby reducing the burden on the environment and increasing the efficiency of fertilizer use. In addition, they make it possible to save work cycles and operating materials, and thereby agricultural costs.

A time-release effect of fertilizers can be achieved in different ways. One possibility is to surround granulated fertilizers that are easily soluble in water with a covering that is insoluble in water. The nutrient release from such coated fertilizers takes place with a delay, since the nutrients must first diffuse through the cover layer before they can be absorbed by the roots. Another possibility is to apply the nutrients in the form of chemical compounds in which they are not available to the plants at first. Only after a prior release step, for example chemical hydrolysis, enzymatic splitting and/or microbial transformation, has taken place, will the nutrients be available in a form that the plants, can utilize. Such fertilizers are also called chemical time-release fertilizers.

The idea of chemical time-release fertilizers dates back to the 19th century. At that time, Liebig in Germany and Murray in England suggested using nutrients in the form of salts with low solubility for plant fertilization.

Today, a large number of substances that contain nitrogen are produced and marketed as time-release fertilizers. The three most important ones, by far, are the condensation products of urea and formaldehyde, isobutyraldehyde, and acetaldehyde.

Other substances that are produced for use as fertilizers on a smaller scale are, among others, oxamide, acetylene diurea, melanine, substituted triazones, and the acetylene diurea shown below.

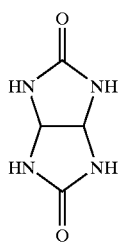

Of these known time-release nitrogen fertilizers, acetylene diurea is of particular interest because of its comparatively high nitrogen content, its very good plant tolerance, as well as its excellent profile of effect. Its synthesis from urea and glyoxal has been described many times. L. Siemonsen reports on the production of acetylene diurea (glycoluril) from glyoxal and urea, with the addition of hydrochloric acid, in *Ann. Chem.* 333, (1904), pages 101 to 111.

The production of acetylene diurea (glycoluril) by means of condensation of glyoxal and urea is described in *Chemistry and Industry,* January 1979, pages 29 to 30 (Glycoluril as a slow-release nitrogen source for plants). For this purpose, solid urea was introduced into 40% glyoxal solution at 70° C., while stirring for 30 minutes. The resulting precipitated solid was filtered off, washed, and dried.

T. Shimizu describes the production of acetylene diurea by means of reacting glyoxal with urea in the presence of an acid as a catalyst in *Soil. Sci. Plant. Nutr.* 33 (1987, pages 291 to 298). To increase the yields, concentration series and variations in the catalyst were carried out. In addition, glyoxal that had not been reacted was passed back into the reaction. In this connection, the reaction was carried out discontinuously, with the glyoxal solution being metered into the urea solution drop by drop, in order to maximize the yield. The yield obtained was 87%. A temperature of 60° C. to 80° C., a reaction time of 1.5 to 3 hours, and a concentration of hydrochloric acid as the catalyst of 5 to 10% are indicated as being optimum reaction conditions. After six feed-back cycles, it was possible to increase the total yield to 91%.

U.S. Pat. No. 3,061,423 describes the use of acetylene diurea (glycoluril) as a fertilizer.

U.S. Pat. No. 2,731,472 relates to the production of heterocyclic compounds of glyoxal and urea, using acidic catalysis. Here, the molar ratio of urea to glyoxal is 2.01 to 2.30. The production takes place discontinuously, and it was possible to feed part of the reaction solution, from which the acetylene diurea was removed, back into the reactor. Before the acetylene diurea that was obtained was filtered off, the solution was neutralized with ammonia.

JP 2001 097974 relates to the production of acetylene diurea by means of the reaction of urea and glyoxal in the presence of hydrochloric acid as a catalyst.

JP 2000 264887 relates to the production of acetylene diurea by means of the reaction of urea and glyoxal, whereby a molar ratio of urea to glyoxal of 2.01 to 2.3 is also adjusted. The work is carried out with saturated urea solution.

JP 2000 290281 relates to the production of acetylene diurea by means of the reaction of urea and glyoxal, whereby urea and glyoxal are continuously metered into a saturated suspension of acetylene urea in a molar ratio of 2.01 to 2.30. Urea and glyoxal are reacted in aqueous solution, in the presence of acid catalyst that is continuously supplied. It is stated that the method allows the continuous production of acetylene diurea.

However, a disadvantage of the known methods is either a discontinuous conduct of the reaction, which is disadvantageous in the production of large amounts, or the use of a larger excess of urea, which must be removed and discarded in the final analysis, or the accumulation of larger amounts of by-products or mother liquor, which must be disposed of.

SUMMARY OF THE INVENTION

It is therefore an object of the present invention to make available a continuous synthesis method for the production of acetylene diurea, which delivers the product at a high yield, while at the same time having a low accumulation of by-products as well as only a low stream of products for disposal.

The above object is accomplished, according to the invention, by means of a method for the continuous production of acetylene diurea by means of the reaction of glyoxal with urea in the presence of mineral acids, in which the reaction is carried out in at least one reactor having a mixing device, into which glyoxal, urea, and mineral acids are continuously fed, and from which a suspension of acetylene diurea in mother liquor is discharged, whereby the acetylene diurea is mechanically removed from the mother liquor, and the remaining mother liquor is recycled back into the reactor, in whole or in part.

In this connection, stirrer vats are preferably used as the reactor or reactors. The reaction partners, glyoxal and urea, are continuously combined in the reactor, particularly the stirrer vat. In parallel, a mineral acid, preferably hydrochloric acid or sulfuric acid, particularly sulfuric acid, is metered in as a catalyst. In this connection, the urea is preferably present in excess, as compared with the glyoxal.

It is particularly preferred in the method according to the invention to use a reactor cascade of at least two stirrer vats that are in series, one behind the other. This allows setting a long dwell time and a narrow dwell time distribution. The total dwell time or residence time in the reactor is preferably 1 to 24 hours, particularly preferably 2 to 8 hours. A dwell time of more than 3 hours is advantageous, in this connection.

The reactor cascade is preferably composed of 2 to 6 stirrer vats, particularly preferably 2 to 3 stirrer vats.

In addition to the reacted reaction mixture, water can be discharged from the reactors, in the form of steam.

The reaction is preferably carried out at a temperature in the range of 50° C. to 90° C., particularly preferably in the range of 60° C. to 80° C., and at a pressure in the range of 0.05 to 1 bar, particularly preferably 0.1 to 0.4 bar.

The acetylene diurea is mechanically removed from the mother liquor. For this purpose, a filtration unit, such as a belt filter, is preferably used. After continuous removal of the precipitated solid, the mother liquor that has been removed is recycled back into the first reactor vat. Therefore only the acids used as the catalyst, particularly sulfuric acid, and the urea excess, which are lost due to the residual moisture that adheres to the product, must be replaced with fresh solutions. As compared to the conventional continuous method of procedure, the need for catalyst acid and urea is significantly reduced.

Preferably, the filter cake obtained on the filtration unit is neutralized by means of treatment with neutralized mother liquor. Preferably, neutralization of the damp filter cake takes place directly on the filtration unit, in that the acidic mother liquor is removed, neutralized, and recycled back to the filtration unit. Preferably, a belt filter is used in this connection. The removed acetylene diurea can be dried in a spin-flash dryer.

According to the invention, the remaining mother liquor is recycled back to the (first) reactor, in whole or in part.

In this connection, it was to be expected that undesirable by-products will slowly become more concentrated and will, in the final analysis, either get into the product, thereby making it impure, or will have to be passed out of the system and disposed of. However, it was found that this is not the case in the method according to the invention, and that instead, the undesirable by-products continue to react until they form the desired product, and contribute to an increased product yield.

The water of reaction that is formed, as well as part of the water entrained with the educts, is preferably evaporated in the reaction. The waste water streams are drastically reduced, they are limited to the residual moisture alone. If the components of the mother liquor are neutralized and accepted in the end product as a secondary component, almost no waste water streams that contain ammonium compounds will occur. Removal can be carried out particularly well on a belt filter. If the residual moisture is removed from the cake, neutralized, and recycled back, no additional unit for neutralization is needed.

DETAILED DESCRIPTION OF PREFERRED EMBODIMENTS

The present invention will now be explained in greater detail by means of the following examples.

EXAMPLE 1

933 g/h urea and 93 g/h sulfuric acid and 1085 g/h (40.3%) glyoxal are continuously placed into a cascade consisting of two stirred vats with a volume of approximately 5 liters each. At the same time, 359 g/h water are continuously evaporated per vat. Evaporation is regulated in such a way that no additional water needs to be introduced into the reactor. The reaction temperature is 65° C., the pressure is approximately 200 mbar. The suspension passed out of the second vat is separated, and the mother filtrate of approximately 1200 g/h is recycled back into the first vat, together with the educts. The yield is >97%. Other than the residual moisture of approximately 15% adhering to the cake, no mother filtrate is passed out of the reaction.

Comparison Example 1

460.5 g/h water, 1492 g/h urea, 444 g/h sulfuric acid, as well as 1085 g/h (40.3%) glyoxal are continuously placed into a cascade consisting of two vats with a volume of approximately 5 liters each. The reaction temperature is 65° C. The yield is 90.5%, and in addition to the residual moisture of approximately 15%, more than 2000 g/h mother liquor occur, which must be disposed of.

Accordingly, while a few embodiments of the present invention have been shown and described, it is to be understood that many changes and modifications may be made thereunto without departing from the spirit and scope of the invention as defined in the appended claims.

What is claimed is:

1. Method for the continuous production of acetylene diurea by reacting glyoxal with urea in the presence of mineral acids, comprising
    carrying out the reaction in at least one reactor having a mixing device, into which glyoxal, urea, and mineral acid are continuously fed; and
    from said reactor discharging a suspension of acetylene diurea in mother liquor;
    mechanically removing the acetylene diurea from the mother liquor; and
    the remaining mother liquor is recycled back into the reactor, in whole or in part.

2. Method according to claim 1, further comprising discharging water in the form of steam from the at least one reactor.

3. Method according to claim 1,
    wherein stirrer vats are used as the reactors.

4. Method according to claim 3,
    wherein a reactor cascade of at least two stirrer vats is used.

5. Method according to claim 1,
    wherein the reaction is carried out at a temperature in the range of 50° C. to 90° C. and at a pressure in the range of 0.05 to 1 bar.

6. Method according to claim 1,
wherein a total residence time in the reactors is 1 to 24 hours.

7. Method according to claim 1,
wherein an excess of urea as compared with glyoxal is present in the reactor.

8. Method according to claim 1, comprising
using a filtration unit for mechanical removal of the acetylene diurea from the mother liquor.

9. Method according to claim 8,
wherein an obtained filter cake is neutralized, on the filtration unit, by means of treatment with neutralized mother liquor.

10. Method according to claim 1, further comprising
drying the removed acetylene diurea in a spin-flash dryer.

* * * * *